United States Patent [19]

Gabridge

[11] Patent Number: 4,952,510

[45] Date of Patent: Aug. 28, 1990

[54] APPARATUS FOR DETECTING AND CULTURING MICROORGANISMS USING A BIPHASIC CULTURE VESSEL

[75] Inventor: Michael G. Gabridge, Saranac Lake, N.Y.

[73] Assignee: Bio-North, Inc., Saranac Lake, N.Y.

[21] Appl. No.: 93

[22] Filed: Jan. 2, 1987

[51] Int. Cl.$^5$ .......................... C12M 1/24; B65D 1/24
[52] U.S. Cl. ..................... 435/296; 220/501
[58] Field of Search ........ 435/287, 292, 293, 296–301, 435/317; 215/6; 220/4 R, 20, 20.5, 21, 22, 82 R

[56] References Cited

U.S. PATENT DOCUMENTS

| | | | |
|---|---|---|---|
| 2,992,974 | 7/1961 | Belcove et al. | 195/139 |
| 3,532,605 | 10/1970 | Riera | 195/139 |
| 3,589,893 | 6/1971 | Holderith et al. | 195/139 |
| 3,702,806 | 11/1972 | Oliva | 195/139 |
| 4,121,976 | 10/1978 | Gleeson | 195/104 |
| 4,308,347 | 12/1981 | Forrer et al. | 435/34 |
| 4,358,539 | 11/1982 | Bittings | 435/301 |
| 4,690,896 | 9/1987 | Brüsewitz et al. | 435/296 |

OTHER PUBLICATIONS

Corner et al., "An Evaluation of a Biphasic Medium for the Isolation of *Brucella Abortus* From Bovine Tissues", *Australian Veterinary Journal*, vol. 62, No. 6, pp. 187–189, (Jun. 1985).
Koshi et al., "Advantages of MacConkey Biphasic Medium for Blood Culture," *Indian Journal of Medical Research*, vol. 81, pp. 584–590, (Jun. 1985).
Henry et al., "Comparison of the Roche Septi-Check Blood Culture Bottle with a Brain Heart Infusion Biphasic Medium Bottle and with a Tryptic Soy Broth Bottle," *Journal of Clinical Microbiology*, vol. 19, pp. 315–317 (Mar. 1984).
Pfaller et al., "Clinical Laboratory Comparison of a Slide Blood Culture System with a Conventional Broth System," *Journal of Clinical Microbiology*, vol. 16, pp. 525–530 (Sep. 1982).
Moody et al., "Evaluation of New Blood Culture Processing Systems," *Journal of Clinical Microbiology*, vol. 20, pp. 351–356 (Sep. 1984).

Primary Examiner—Christine M. Nucker
Assistant Examiner—T. J. Wallen
Attorney, Agent, or Firm—Heslin & Rothenberg

[57] ABSTRACT

A biphasic culturing apparatus which employs multiple solid nutrient media in a single vessel includes an enclosed container which has an opening defined in one of its surfaces for introducing material into the container. At least one container surface includes a flat, transparent portion for viewing the solid and liquid nutrient media from outside the container. A first partition inside the container divides the interior volume thereof into upper and lower portions, and at least one second partition divides the upper container portion into a plurality of compartmental volumes. A liquid nutrient medium is located in the lower container portion, and a solid nutrient medium is contained in each compartmental volume. The first and second partitions are configured so that each solid nutrient medium may be separately innoculated with the liquid medium.

33 Claims, 4 Drawing Sheets

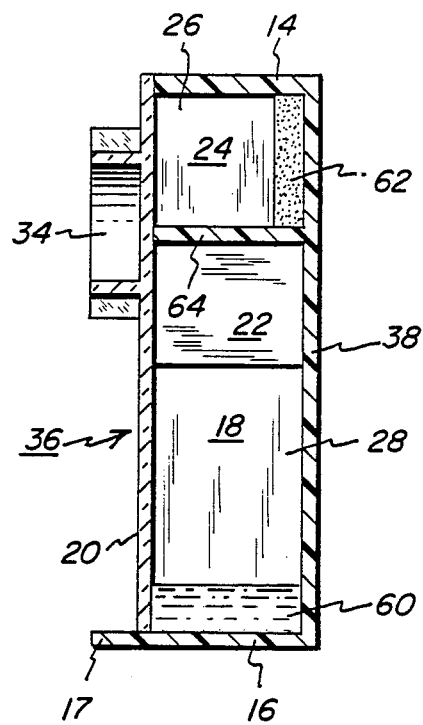
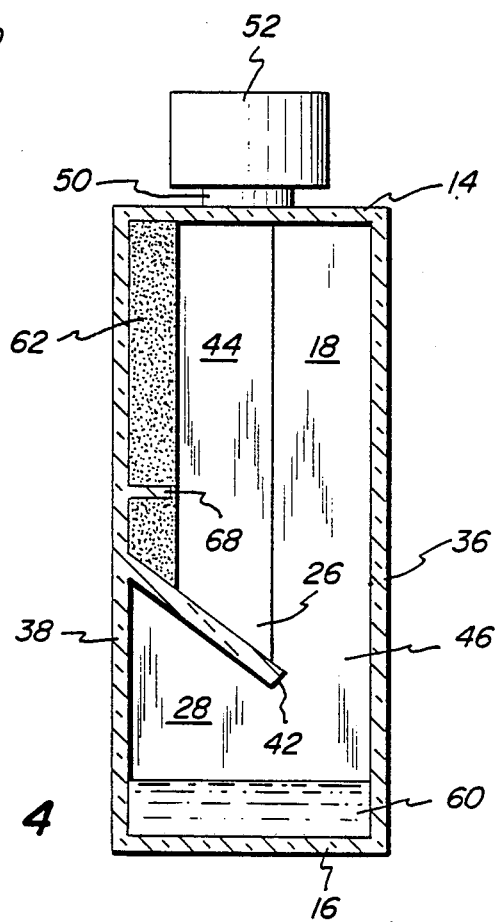

APPARATUS FOR DETECTING AND CULTURING MICROORGANISMS USING A BIPHASIC CULTURE VESSEL

BACKGROUND OF THE INVENTION

This invention relates to culturing microorganisms in a culture vessel having both liquid and solid nutrient media. More particularly, it relates to a culture vessel in which two or more different solid nutrient media are easily separable from a liquid nutrient medium, which solid media can be selectively inoculated with the liquid nutrient medium without opening the vessel.

Microorganisms can be cultured either in a liquid nutrient medium, which is often referred to as a "broth," or on the surface of a nutrient medium which has been solidified with a gelling agent such as agar-agar, which medium is often referred to as either an "agar" or an "agar slant." Each culturing medium offers its own advantages. When cultured in a liquid nutrient medium, a single microbe will theoretically propagate a population of sufficient density to cause visible turbidity in the liquid medium within approximately 24 to 72 hours. When cultured on an agar medium, a single microbe of an input microorganism which is physically separate and immobile can develop into a visible colony which is clonogenic, quantifiable, and relatively easy to subculture. Since each of these types of culturing offers its own advantages, in many biological tests both culturing methods are employed By way of example, such culturing is commonly used when examining blood specimens for the presence of a variety of microorganisms, both aerobic and anaerobic, including brucella, salmonella, and many types of bacteria and fungi.

Typically, to detect microorganisms in a fluid sample, the sample is used to inoculate a liquid nutrient medium. Subsequently, the liquid medium is, in turn, used to inoculate a solid medium in order to grow a colony of the microorganisms. In order to obviate the need for accomplishing a troublesome and potentially dangerous transfer of the liquid medium preculture to the solid culture medium, from one container to another, culture vessels have been developed in which both the liquid and the solid culture media are contained in the same vessel. Because these vessels contain both solid and liquid media, they have come to be known as "biphasic." Generally, the sample to be tested is introduced into a liquid broth, and the culture vessel is then manipulated so as to mix the sample with the broth and also to wash the mixture over the solid nutrient medium surface. The vessel is usually then positioned so that the two media are separated and the media are incubated to allow colony growth. After a suitable incubation period, the solid and liquid nutrient media may be examined for the presence and/or growth of the suspect microorganisms.

An optimum biphasic culture vessel should meet several requirements and should provide solutions for a number of problems encountered by the culture vessels of the prior art The culture vessel must provide a means for keeping the liquid medium separated from the solid medium during transportation, storage, and use of the vessel, while at the same time allowing contact to be made between the liquid and solid media by appropriately manipulating the culture vessel. If the liquid and solid media are not separated during storage and use, the solid medium can dissolve into the liquid medium. At the very least, this mixing of the solid and liquid media can make differentiation of the pathogens difficult, and in some cases, mixing of the two media can produce hazardous conditions. At the same time, the culture vessel should be configured so as to facilitate microscopic examination of colonies growing on the solid nutrient medium, by looking through one or more of the culture vessel's walls. Also, the solid nutrient medium, being formed from a gelatinous material, is relatively easily dislodged from its mounting surface. Accordingly, the culture vessel should include means for retaining the solid nutrient medium in its proper position. Furthermore, the vessel should be designed so that the entire assembly can be sterilized by autoclaving after the solid and liquid nutrient media have been added to the vessel. For efficiency in performing multiple tests in a single vessel, it is also desirable that the culture vessel contain multiple solid nutrient media.

A number of culture vessels have been described in the prior art which address some of the requirements outlined above, but none of the vessels disclosed simultaneously provide all of these features U.S. Pat. No. 2,992,974, issued July 18, 1961 to A. S. Belcove et al., describes a biphasic culture vessel which includes a number of mechanisms for holding the agar slant in position within the vessel U.S. Pat. No. 3,532,605, issued Oct. 6, 1970 to J. V. Riera, describes a similar vessel in which a mesh is embedded in the solid nutrient material in order to further strengthen the agar slant. However, neither of the culture vessel assemblies described in those patents can be sterilized by autoclaving. For both of them, heating of the solid nutrient material would cause it to melt and become mixed with the liquid nutrient medium. Furthermore, for both of these culture vessel designs, the vessel must be placed in a generally horizontal position in order to separate the solid and liquid nutrient media during incubation. Then, in order to examine the surface of the solid nutrient medium for colony growth, the vessel must be placed in a generally upright position, thereby allowing the liquid medium to again contact the solid medium and to disturb the newly grown microorganism colonies.

U.S. Pat. No. 3,702,806, issued Nov. 14, 1972 to W. E. Oliva, discloses a culture vessel having a similar configuration to that described in the patent to Riera. In place of the cylindrical or rectangular vessel shown in the patent to Riera, the patent to Oliva discloses a vessel having a triangular cross-section. Oliva also discloses employing multiple agar slants, with different agars being mounted on each of the three surfaces which form the triangular cross-section. However, this culture vessel suffers the same inadequacies in sterilization capability and viewability as where noted above for the culture vessels described by Riera and Belcove et al.

A culture vessel which provides improved agar retention, media separability, and the capability of being sterilized by autoclaving is disclosed in U.S. Pat. No. 4,121,976, issued Oct. 24, 1978 to C. M. Gleeson. However, in the culture vessel shown in that patent, only one solid nutrient medium can be used in each vessel. The culture vessels described in U.S. Pat. No. 3,589,983, issued June 29, 1971 to W. J. Holderith et al., and in U.S. Pat. No. 4,308,347, issued Dec. 29, 1981 to H. Forrer et al., each may employ more than one solid nutrient medium in a single vessel. However, each of the vessels disclosed uses a two-piece design that is relatively complex and expensive to manufacture. The culture vessel of Forrer et al. also requires connecting the two portions of the vessel during use, which can easily lead to contamination of the culturing media.

What is needed, then, is a biphasic culture vessel which can employ two or more solid nutrient media, each of which can be inoculated separately by simple manipulation of the vessel. The liquid should be separated from the solid media during transportation, storage, and incubation. The vessel should be configured so that the entire assembly may be sterilized by an autoclaving process after the solid and liquid nutrient media have been deposited inside the vessel. The vessel should be further configured so that colonies of microorganisms growing on the solid nutrient media can be examined with an ordinary microscope. The vessel design should provide retention of the solid nutrient media in their positions within the vessel, while also facilitating subculturing of the microorganism colonies growing on the solid nutrient media. Finally, the vessel should be constructed of a relatively simple one-piece design which is inexpensive to manufacture and easy to use.

Accordingly, it is an object of the present invention to provide a biphasic culturing apparatus containing multiple solid nutrient media which are easily separable from the liquid nutrient medium during shipping, storage, and usage of the culturing apparatus.

It is also an object of the present invention to provide a biphasic culturing apparatus in which each solid nutrient medium can be separately inoculated by simple manipulation of the culturing apparatus, without opening the culture vessel.

It is another object of this invention to provide a culturing apparatus in which the solid nutrient media are sufficiently retained in position so that they are not dislodged during shipping or usage of the apparatus.

It is a further object of the instant invention to provide a culturing apparatus which is configured so that colonies of microorganisms growing on the solid nutrient media may be examined using an ordinary laboratory microscope, without opening the culture vessel.

It is still another object of the present invention to provide a biphasic culture vessel design which is simple and inexpensive to manufacture.

It is likewise an object of this invention to provide a method of detecting microorganisms in which multiple tests are concurrently conducted using a single culture vessel which contains multiple solid nutrient media.

It is another object of the present invention to provide a method for biphasic culturing of microorganisms wherein each solid nutrient medium may be separately inoculated with the liquid nutrient medium by tilting the culture vessel at a predetermined angle.

It is a further object of the instant invention to provide a method for preparing a biphasic culturing apparatus wherein the solid and liquid nutrient media may be sterilized either by aseptically depositing the media into a previously sterilized culture vessel, or by autoclaving the entire culturing apparatus after the solid and liquid nutrient media have been placed in the vessel.

It is also an object of the present invention to provide a method of culturing microorganisms in either an aerobic or an anaerobic environment.

SUMMARY OF THE INVENTION

In accordance with one aspect of the present invention, a culture vessel comprises an enclosed container which is formed by a top surface, a bottom surface, and a side surface which connects the top surface to the bottom surface. The bottom surface is disposed so that the container is supported thereon in a stable manner when the container is placed in an upright position. One of the container surfaces has defined therein an opening for introducing material into the interior of the container. At least one of the container surfaces also includes a portion which is formed from a flat, transparent material through which at least a portion of the volume enclosed by the container may be viewed from outside the container. The culture vessel also comprises a first partition and at least one second partition, each of which is located inside the container. The first partition is disposed so as to divide the interior volume of the container into an upper portion and a lower portion, and the second partitions are disposed so as to divide the upper container portion into a plurality of compartmental volumes. The first and second partitions are configured with respect to the transparent surface portion so that at least a portion of each compartmental volume may be viewed from outside the container. Preferably, at least a portion of the lower container volume is also viewable through the transparent surface. The first and second partitions are disposed with respect to the container opening so that material may be introduced into at least the lower portion of the container. Preferably, material may also be introduced into each of the compartmental volumes. The first and second partitions are further disposed with respect to the side surface of the container so that liquid located in the lower container portion is introduced into preselected compartmental volumes by tipping the container at a predetermined angle with respect to its upright position. Preferably, the first and second partitions are further disposed so that liquid located in any of the compartmental volumes drains into the lower container portion when the container is placed in its upright position. The culture vessel of the present invention may further comprise means for sealing the container opening so that material is prevented from entering or leaving the interior of the container.

In accordance with another aspect of the present invention, an apparatus for detecting and culturing microorganisms includes a culture vessel of the type described above, and further comprises a liquid nutrient medium and a plurality of solid nutrient media. The liquid nutrient medium is disposed in the lower container portion, and one of the solid nutrient media is located in each compartmental volume. The solid nutrient media are disposed so that at least a portion of each one is viewable through the transparent portion of the container, and so that, when the liquid nutrient located in the lower container portion is introduced into a preselected compartmental volume by tipping the container at the appropriate predetermined angle, the liquid nutrient makes contact with the solid nutrient medium contained in that compartmental volume. The culturing apparatus of the present invention may also include means for holding each solid nutrient medium in position within its associated compartmental volume.

In accordance with a third aspect of the present invention, a method for preparing a microbiological culturing apparatus comprises providing a culture vessel of the type described above, and depositing a plurality of preselected culturing base materials into the compartmental volumes of the vessel. The culturing base materials are selected from compositions which are solid at culturing temperatures and molten at elevated temperatures One of these preselected materials is located in each of the compartmental volumes. The culture vessel is positioned so that, when the culturing base material deposited into each compartmental volume is in its molten state, the base material forms a molten agar slant having a predetermined shape and location The preparation method of the present invention also comprises heating the culturing base materials to their molten states, and then cooling the resulting molten agar slants until the culturing base materials solidify. The heating step may be carried out either before the culturing base materials are deposited into the compartmental volumes, or afterward. The preparation method may further include placing the culture container in the upright position and depositing a liquid nutrient medium into the lower portion of the container.

In accordance with yet another aspect of the present invention, a method for detecting microorganisms in a specimen comprises providing a biphasic culturing apparatus of the type described above and introducing a specimen containing the microorganisms into the liquid nutrient medium. The solid nutrient media disposed in the preselected compartmental volumes are then each contacted by the liquid nutrient medium by tipping the container at the appropriate predetermined angle. The solid nutrient media are incubated for a time sufficient for suitable growth of the microorganisms, and the presence of microorganisms on the solid nutrient media is then determined, preferably by microscopic examination. If desirable, the mixture of the liquid nutrient medium and the sample containing the microorganisms may be incubated for a predetermined period of time before the solid nutrient media are contacted with this mixture. The culturing method of the present invention may also include determining the growth of microorganisms in the liquid nutrient medium.

BRIEF DESCRIPTION OF THE DRAWINGS

The subject matter which is regarded as the invention is particularly pointed out and distinctly claimed in the concluding portion of the specification. The invention itself, however, both as to its organization and its method of practice, together with further objects and advantages thereof, may best be understood by reference to the following description taken in conjunction with the accompanying drawings, in which:

FIG. 2 is a side elevation, cross-sectional view of the apparatus shown in FIG. 1, taken along line 2—2, in which view the solid and liquid nutrient media which were omitted from FIG. 1 are shown in their respective locations;

FIG. 4 is a side elevation, cross-sectional view of the apparatus shown in FIG. 3, taken along line 4—4, in which view the solid and liquid nutrient media which were omitted from FIG. 3 are shown in their respective locations.

DETAILED DESCRIPTION OF THE PREFERRED EMBODIMENTS

Figure 1:
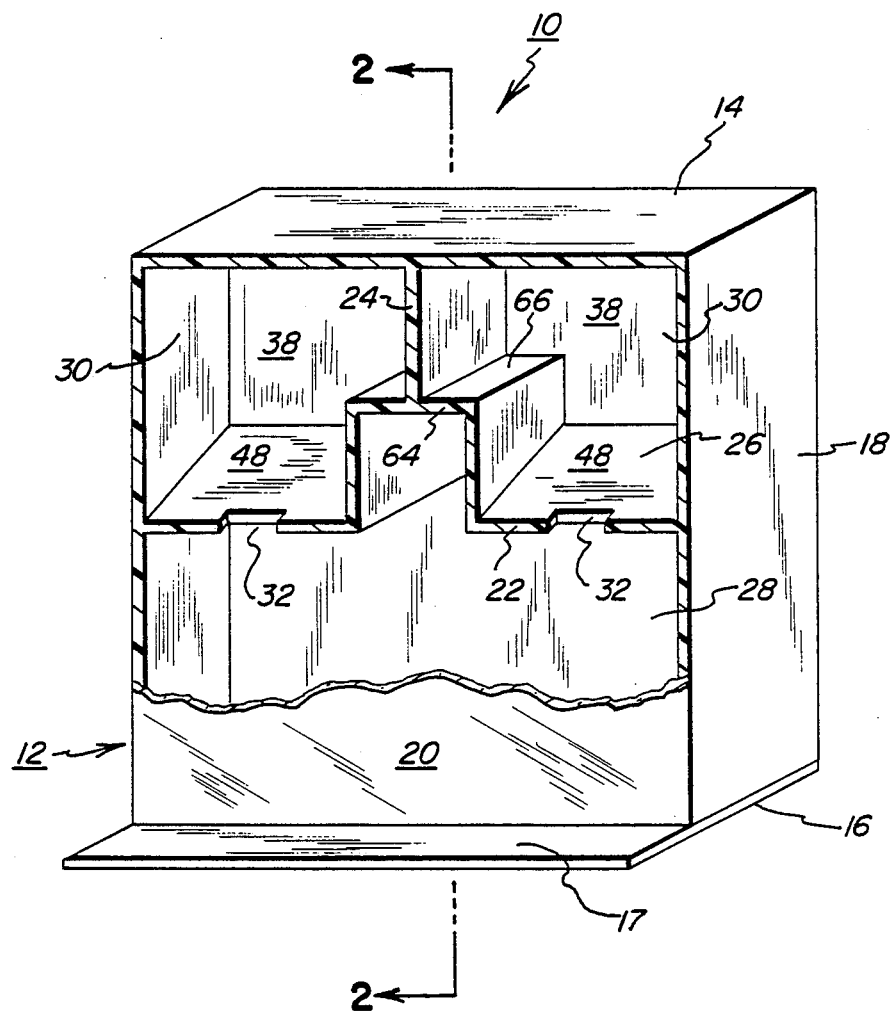
FIG. 1 is a perspective view in partial cross-section schematically illustrating one embodiment of an apparatus for detecting and culturing microorganisms in accordance with the present invention, in which view the solid and liquid nutrient media have been omitted for the sake of clarity.

FIG. 1 schematically illustrates a culture vessel in accordance with the present invention which is particularly useful for biphasic culturing of microorganisms. Culture vessel 10 comprises enclosed container 12 which is formed by top surface 14, bottom surface 16, and side surface 18. Side surface 18 serves to connect top surface 14 and bottom surface 16 together in order to form enclosed container 12. Bottom surface 16 is disposed so as to stably support container 12 when container 12 is placed in the upright position shown in FIG. 1. In the particular embodiment illustrated therein, bottom surface 16 includes lip 17 which further stabilizes container 12 when it is supported on surface 16. At least one of surfaces 14, 16, and 18 include a portion which is formed from a flat, transparent material, in the manner illustrated in FIG. 1 by transparent surface 20, through which at least a portion of the volume enclosed by container 12 is viewable from outside culture vessel 10.

Located inside container 12 are first partition 22 and at least one second partition 24. First partition 22 is disposed between top surface 14 and bottom surface 16 so as to divide the volume enclosed by container 12 into upper portion 26 and lower portion 28. Each second partition 24 is disposed so as to divide upper container portion 26 into a plurality of compartmental volumes 30. First and second partitions 22 and 24 are configured with respect to transparent surface 20 so that at least a portion of each compartmental volume 30 is viewable through surface 20.

Figure 5:
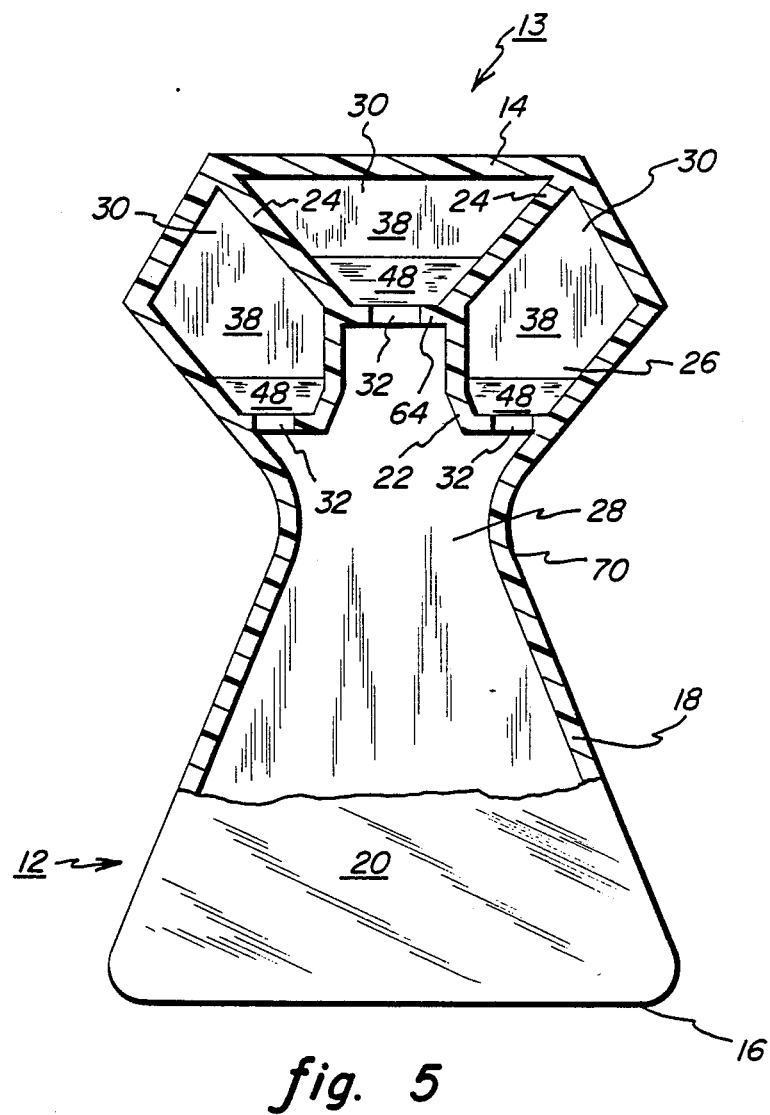
FIG. 5 is a side elevation view in partial cross-section schematically illustrating a third embodiment of an apparatus for detecting and culturing microorganisms in accordance with the present invention, in which view the solid and liquid nutrient media have again been omitted for the sake of clarity.

An embodiment of the present invention which is similar to that shown in FIG. 1 is schematically illustrated in FIG. 5. Culture vessel 13 again comprises container 12 which is formed from top surface 14, bottom surface 16, and side surface 18. Side surface 18 includes flat, transparent section 20 through which the interior of container 12 may be viewed from outside culture vessel 13. First partition 22 divides the volume enclosed by container 12 into upper and lower portions 26 and 28. In the embodiment of FIG. 5, however, two second partitions 24 are employed in order to divide upper container portion 26 into three compartmental volumes 30. Culture vessel 13 also provides two other features which are not illustrated in the embodiment of FIG. 1. In the embodiment shown in FIG. 5, side surface 18 is disposed so that the cross-sectional area of lower container portion 28, for a cross-section taken through side surface 18 in a plane substantially parallel to bottom surface 16, generally decreases as the distance between bottom surface 16 and the cross-sectional plane increases. With side surface 18 so configured, lower container portion 28 is narrower at its uppermost portion than at its lowermost portion. The result of this narrowing of lower container portion 28 is that liquid located therein is restrained from splashing upwardly toward compartmental volumes 30. Side surface 18 may be further disposed so as to provide a means for grasping container 12. In the embodiment illustrated in FIG. 5, side surface 18 includes curved surface portion 70 which provides a generally v-shaped exterior portion for container 12, by which portion container 12 is easily grasped.

First and second partitions 22 and 24 are further disposed so that liquid located in lower container portion 28 is introduced into preselected ones of compartmental volumes 30 by tipping container 12 at a predetermined angle with respect to its upright position. In the embodiments illustrated in FIGS. 1 and 5, first partition 22 has defined therein a plurality of openings 32 located so that at least one opening 32 is associated with each compartmental volume 30. When container 12 is placed in the appropriate position, liquid located in lower container portion 28 flows through preselected ones of openings 32 and into the associated compartmental volumes 30. In FIGS. 1 and 5, openings 32 are shown located in the portion of first partition 22 which is situated closest to transparent section 20. With openings 32 so configured, culture vessels 10 and 13 may be placed in a generally horizontal position, with transparent section 20 facing upwardly, without liquid located in lower container portion 28 accidentally entering compartmental volumes 30. If, in a particular application, culture vessels 10 and 13 are not usually placed in such a horizontal position, openings 32 could be located in other portions of partition 22 without effecting the functional characteristics of vessels 10 and 13.

Figure 3:
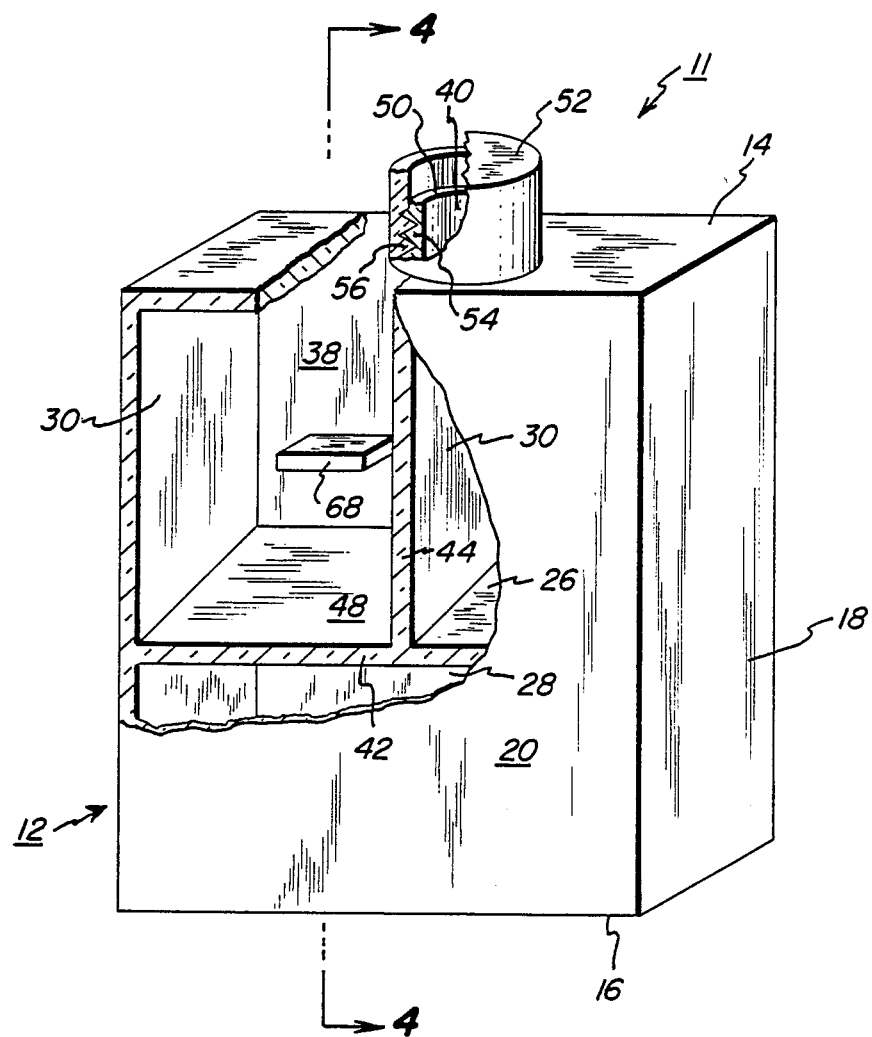
FIG. 3 is a perspective view in partial cross-section schematically illustrating a second embodiment of an apparatus for detecting and culturing microorganisms in accordance with the present invention, in which view the solid and liquid nutrient media have again been omitted for the sake of clarity.

The culture vessel of the present invention also includes an opening defined in one of the surfaces which form container 12, through which opening material may be introduced into the interior of container 12. This container opening is located with respect to first and second partitions 22 and 24 so that material may be introduced through the opening into lower container portion 28. As is schematically illustrated in FIG. 2, which is a cross-sectional view of FIG. 1 taken along line 2—2, in one embodiment, container opening 34 is located in side surface 18 of container 12. Although not shown in the view of FIG. 5, culture vessel 13 includes a container opening disposed in the same manner as container opening 34 shown in FIG. 2. In an alternative embodiment of a culture vessel in accordance with the present invention, which is schematically illustrated in FIG. 3, the container opening is located in the top surface of the container, in the manner shown in FIG. 3 by container opening 40. In both of the embodiments shown, the container opening is further disposed so that material may be introduced therethrough into preselected compartmental volumes 30 or into lower container portion 28 without entering nonselected portions of container 12. With container opening 34 located in the manner shown in FIG. 2, material may be added to the selected portions of container 12 especially easily by placing container 12 in a horizontal position with transparent section 20 facing upwardly.

Although not shown in the Figures, the embodiment of the culture vessel of the present invention illustrated in FIGS. 3 and 4 may further comprise a channel for directing liquids from container opening 40 to lower container portion 28. The liquid-directing channel is disposed so that one end thereof is connected in flow communication with opening 40 and the other end thereof opens into lower container portion 28. For the culture vessel illustrated in FIGS. 3 and 4, this channel may conveniently comprise a tube which extends from opening 40 along the interior of transparent surface 20 into lower container portion 28.

Similarly to the culture vessels shown in FIGS. 1 and 5, the culture vessel embodied by FIGS. 3 and 4 comprises container 12 formed from top, bottom, and side surfaces 14, 16, and 18, respectively, one of which surfaces includes a flat, transparent portion of the type shown in FIG. 3 by transparent surface 20. First and second partitions 42 and 44 again divide the interior of container 12 into upper and lower portions 26 and 28, respectively, and thereby form a plurality of compartmental volumes 30 in the same manner as was described above in relation to FIG. 1. As is illustrated in FIG. 4, partition 42 is further disposed so that the edge thereof which is located closest to transparent section 20 is separated from section 20 by one or more openings 46. Openings 46 are configured so that when culture vessel 11 is tipped at a predetermined angle with respect to its upright position, liquid located in lower container volume 28 flows through openings 46 and into preselected ones of compartmental volumes 30.

For each of culture vessels 10, 11, and 13, transparent section 20 is included in side surface 18 and is disposed so that at least a portion of lower container volume 28 and at least a portion of each compartmental volume 30 is viewable through transparent section 20. In the embodiments shown, side surface 18 is comprised of front surface 36 and back surface 38. At least a portion of front surface 36 comprises a flat, transparent material so as to form transparent section 20. For optimum viewability of the interior of the culture vessel, all of front surface 36 may be made from a transparent material. For the culture vessels shown, front and back surfaces 36 and 38 are configured so as to be substantially parallel to each other, and container 12 is configured so that a cross-section taken through side surface 18 in a plane substantially parallel to bottom surface 16 is generally rectangular in shape. However, containers having other cross-sectional shapes may also be used to form a culture vessel in accordance with the present invention. For example, a container having a trapezoidal cross-section may be employed, as well as a container whose back surface has a semi-circular cross-section. Containers having a rectangular or trapezoidal cross-section offer the advantage of providing a stable support surface when the culture vessel is placed in a horizontal position with transparent section 20 facing upwardly.

For the culture vessel of the present invention, the first and second partitions may be disposed generally perpendicularly with respect to each other, in the manner illustrated by FIGS. 1 and 3, or at some other convenient angle, in the manner illustrated in FIG. 5. In each of culture vessels 10, 11, and 13, the first and second partitions are further disposed so that, when container 12 is supported on bottom surface 16 in its upright position, liquid located in compartmental volumes 30 drains into lower container portion 28. In the embodiments shown, liquid drains out of compartmental volumes 30 by passing through openings 32 and 46, respectively, which are the same openings that are employed for introducing liquid nutrient medium from lower container portion 28 into compartmental volumes 30 for inoculation of the solid nutrient media. In order to further facilitate drainage of liquids from compartmental volumes 30, the portion of the first partition which forms the bottom wall of each compartmental volume 30 may be disposed so as to extend toward transparent section 20 at a downward angle. With the first partition so configured, the bottom wall of each compartmental volume 30 slants toward bottom surface 16 of container 12 in the manner illustrated in FIGS. 1-5 by slanting surfaces 48.

Culture vessels 10, 11, and 13 may further comprise means for sealing the container opening so that material is prevented from passing through the container opening into or out of the interior of container 12. FIG. 3 schematically illustrates one embodiment of such a sealing means. As shown therein, the container opening and sealing means may comprise neck portion 50 and sealing cap 52. Cap 52 is sealingly engaged with neck portion 50 by means of threaded surface 54 disposed around the outer circumference of neck portion 50 and cooperating threaded surface 56 disposed around the inner circumference of cap 52. Neck portion 50 is disposed in surface 14 so as to form a passageway between the interior of container 12 and the exterior thereof. When sealing cap 52 is engaged with neck portion 50, materials such as fluids are prevented from passing into or out of container opening 40. In an alternative embodiment to that shown in FIG. 3, threaded surface 54 of neck portion 50 may be replaced by a sealing ridge which extends around the outer circumference of neck portion 50, and threaded cap 52 may be replaced with a snap-on cap whose inner surface mates with the sealing ridge. In yet another embodiment, a resilient stopper, such as a stopper made from rubber or some other elastomeric material, may be sealingly engaged against the interior surface of neck portion 50.

Culture vessels 10, 11, and 13 may be manufactured from any suitable material. Preferably, at least front surface 36 is made from a transparent material such as glass or a clear plastic. For economy of manufacture, a moldable plastic such as polycarbonate or polystyrene may be employed.

The culture vessel of the present invention may be used for general microbiological isolations with all types of input samples, including swabs, solids, liquids, cells, etc. With an appropriately shaped baffle placed in the container opening, the culture vessel could even be used to collect specimens, such as urine samples, directly into the culture vessel without mediation through any additional containers. One particularly useful application for the culture vessel of the present invention is for use as an apparatus for detecting and culturing microorganisms. In such an application, a liquid nutrient medium is disposed in lower container portion 28, in the manner illustrated in FIGS. 2 and 4 by liquid nutrient medium 60. A solid nutrient medium is located in each compartmental volume 30 in the manner illustrated by solid nutrient medium 62 shown in FIGS. 2 and 4. The solid nutrient medium located in each compartmental volume 30 is disposed so that at least a portion of it is viewable through transparent section 20, and so that liquid nutrient medium introduced into compartmental volume 30, by tipping container 12 at the appropriate predetermined angle, makes contact with the solid nutrient medium contained in associated compartmental volume 30. As will be further described hereinbelow, it is convenient to form solid nutrient media 62 so that they are disposed adjacent to back surface 38 of container 12. However, with solid nutrient media 62 disposed in a vertical position against back surface 38, media 62 have a tendency to slip downwardly along surface 38. Thus, for the embodiments of the present invention illustrated in FIGS. 1-5, it is preferable that the culturing apparatus also include means for holding solid nutrient media 62 in position relative to back surface 38. One such holding means is illustrated in FIG. 1. In the culturing apparatus shown therein, first partition 22 includes a bridge-like portion 64. When a solid nutrient medium is placed against back surface 38 within compartmental volume 30, a portion of the lower edge of the solid nutrient medium rests against surface 66 of bridge-like portion 64 of partition 22. This abutment of the lower edge of the solid nutrient medium against surface 66 tends to prevent the solid nutrient medium from slipping downwardly along surface 38. In a similar manner, for the culture vessel of FIG. 5, solid nutrient media (not shown) disposed adjacent to back surface 38 are restrained in position with respect thereto. Second partitions 24 and side surface 18 provide each of compartmental volumes 30 with angled surfaces which tend to prevent the solid nutrient media from slipping downwardly along surface 38. In an alternative embodiment which is illustrated in FIGS. 3 and 4, the holding means comprises a plurality of anchoring bars 68 which are formed as an integral part of back surface 38 and which extend toward front surface 36 for a predetermined distance into the solid nutrient medium located in each compartmental volume 30. Anchoring bars 68 are located so that at least one of them is associated with each solid nutrient medium. Of course, anchoring bars similar to those shown in FIG. 3 could also be employed in the embodiments illustrated in FIGS. 1 and 5.

In order to prepare a microbiological culturing apparatus, it is generally necessary to introduce appropriate quantities of suitable solid and liquid nutrient material into a culture vessel in such a manner that the desired biphasic apparatus is formed. In accordance with the present invention, a method for preparing a biphasic microbiological culturing apparatus comprises providing a culture vessel of the type illustrated in FIGS. 1, 3, and 5 and described hereinabove in relation thereto. A plurality of preselected culturing base materials are deposited into compartmental volumes 30 of container 12, with one of the preselected materials being located in each compartmental volume 30. The preselected culturing base materials are chosen from compositions which are solid at culturing temperatures and molten at elevated temperatures. Container 12 is positioned so that, when the culturing base material which is deposited into compartmental volume 30 is in its molten state, the base material forms a molten agar slant having a predetermined shape and location within compartmental volume 30. The predetermined shape and location of the agar slant are such that at least a portion of each agar slant is viewable through transparent surface 20, and such that each agar slant may be inoculated with the liquid nutrient medium by appropriate manipulation of container 12. Each culturing base material is heated to its molten state, whereupon the material flows into a smooth layer in response to the force of gravity. The culturing base materials may be heated before they are deposited into compartmental volumes 30, or they may be first deposited in compartmental volumes 30 in a solid state and then heated to a molten state. Regardless of whether the base materials are heated before or after they are deposited into compartmental volumes 30, it is preferable that container 12 be positioned so that the top surface of the molten agar slant forms a plane which is parallel to the plane which contains flat, transparent section 20. With container 12 so positioned, the agar surfaces which are utilized for growing colonies of microorganisms are parallel to transparent section 20, thereby minimizing optical aberrations which might otherwise occur when the microorganism colonies are examined using a microscope located outside of the culture vessel. In order to provide this feature in the culturing apparatus shown in FIGS. 1-5, culture vessels 10, 11, and 13 are each supported on back surface 38 in a generally horizontal position during the heating step. With vessels 10, 11, and 13 in this position, molten culturing base material located in each compartmental volume 30 forms a uniformly thick agar layer disposed against the interior of back surface 38. By appropriately choosing the composition and quantity of base culturing material which is deposited into each compartmental volume 30, agar slants having not only different compositions but also different thicknesses may be formed.

The molten agar slants formed in compartmental volumes 30 as a result of these depositing, positioning, and heating steps are then cooled until the associated culturing base materials solidify. The culturing apparatus preparation method of the present invention may further comprise placing container 12 in its upright position and depositing an appropriate quantity of a suitable liquid nutrient medium into lower container portion 28.

It is often advantageous to heat the culturing base materials to a temperature sufficient to sterilize them. If the culture vessel being used is formed from a material which cannot withstand the temperatures employed in autoclaving processes, the culture vessel can be sterilized using a non-heating process. The base culturing materials and the liquid nutrient medium can each be sterilized using any suitable method, and can then be introduced aseptically into the previously sterilized culture vessel. If the culture vessel is made from a material which can withstand autoclaving temperatures, it is often more convenient to deposit the base culturing materials and the liquid nutrient medium into the culture vessel, position the vessel to obtain the desired agar slants, and then autoclave the entire apparatus.

Once the culturing apparatus has been prepared in accordance with the method described above, the apparatus may be used to detect microorganisms in a specimen. In accordance with the present invention, a method for doing so comprises providing a biphasic culturing apparatus of the type described hereinabove in relation to FIGS. 2 and 4. The specimen to be tested is then introduced into the liquid nutrient medium of the biphasic culturing apparatus. The mixture of the specimen and the liquid nutrient medium is then contacted to the solid nutrient media disposed in preselected ones of the compartmental volumes, by tipping the culture vessel at one or more predetermined angles. The solid nutrient media are then incubated for a time sufficient for suitable growth of the microorganisms, and the presence of microorganisms on the solid nutrient media is determined. When the culture vessels embodied by FIGS. 1-5 are utilized, the incubation may be carried out with the culture vessel in either its upright position or in a horizontal position while being supported on back surface 38. However, to facilitate drainage of the liquid nutrient medium from compartmental volumes 30 after the liquid nutrient medium is used to inoculate the solid nutrient media, vessels 10, 11, and 13 should be placed in their upright positions for a short period of time following the inoculation step. If the presence of microorganisms on the solid nutrient media is to be determined by microscopic examination of the agar surfaces, it is convenient to examine the agar surfaces with the vessels supported on back surface 38 in a generally horizontal position With vessels 10, 11, and 13 in either an upright or a horizontal position, the liquid and solid media are separated, and the liquid nutrient medium will not obscure observation of colonies of microorganisms growing on the solid nutrient media. This feature is particularly important for conducting testing where either the liquid nutrient medium or the specimen being tested is substantially opaque.

The microorganism detection method of the present invention may further comprise determining the growth of microorganisms in the liquid nutrient medium. Furthermore, if it is desirable for a particular application, the mixture of the specimen and the liquid nutrient medium may itself be incubated for a predetermined period of time before the mixture is used to inoculate the solid nutrient media.

For a number of applications, it is desirable to provide control over the incubation environment inside the culture vessel. For those applications, the culturing apparatus further includes closable means for sealing container 12 so that material is prevented from entering or leaving the interior of the culture vessel, and the method of the present invention further comprises closing the sealing means after introducing the specimen into the liquid nutrient medium. Utilizing this embodiment of the present invention, testing may be conducted under either aerobic or anaerobic conditions. If anaerobic incubation is to be conducted, the air contained in the culture vessel may be completely evacuated and supplanted by nitrogen, carbon dioxide, some other gas whose presence is desired for the particular testing involved, or combinations thereof.

The foregoing describes a biphasic culturing apparatus which contains multiple solid nutrient media in a single vessel. The liquid nutrient medium can easily be separated from the solid nutrient media, and can be selectively placed in contact therewith by simple positioning of the vessel. The present invention provides a culturing apparatus design which is simple and inexpensive to manufacture, while also being configured so that colonies of microorganisms growing on the solid nutrient media may be examined using an ordinary laboratory microscope. The culturing apparatus design also provides sufficient retention of the solid nutrient media in position within the culture vessel so that the solid nutrient media are not dislodged during shipping or usage of the apparatus. The present invention also provides a method for preparing a biphasic culturing apparatus wherein the solid and liquid nutrient media may be introduced into the culture vessel and the entire assembly may be sterilized by an autoclaving process. The present invention further provides a method for detecting microorganisms in a specimen by conducting multiple tests in a single culture vessel. The testing may be carried out in either an aerobic or an anaerobic environment.

While the invention has been described in detail herein in accord with certain preferred embodiments thereof, many modifications and changes therein may be effected by those skilled in the art. Accordingly, it is intended by the appended claims to cover all such modifications and changes as fall within the true spirit and scope of the invention.

The invention claimed is:

1. A culture vessel comprising:
   a container formed by a top surface, a bottom surface disposed so as to stably support said container when said container is placed in an upright position, and a side surface which connects said top surface to said bottom surface, with one of said surfaces having a sealable opening defined therein for introducing material into the volume enclosed by said container, at least one of said surfaces further including a portion which is formed from a flat, transparent material;

a first partition disposed inside said container between said top and bottom surfaces so as to divide the volume enclosed by said container into an upper portion and a lower portion; and at least one second partition disposed inside said container so as to divide said upper portion of said container into two or more compartmental volumes, said first partition having at least one opening therein between said lower portion and each of said upper compartmental volumes, allowing communication between said lower portion and said upper compartmental volumes, said first and second partitions being configured with respect to said flat, transparent surface portion and to said container opening so that at least a portion of each said compartmental volume is viewable through said transparent surface portion and so that material may be introduced through said opening into said lower portion of said container, and said first and second partitions, said side surfaces and the openings in said first partition all being further disposed so that liquid located in said lower container portion is introduced into preselected ones of said compartmental volumes by tipping said container at a predetermined angle with respect to said upright position so that such liquid will still through the at least one opening associated with each such preselected volume.

2. The culture vessel of claim 1 wherein said transparent surface portion is included in said side surface of said container and is disposed so that at least a portion of said lower container volume and at least a portion of each said compartmental volume is viewable through said transparent surface portion.

3. The culture vessel of claim 1 wherein said transparent surface is in said side section.

4. The culture vessel of claim 3 wherein said container is further configured so that a cross-section taken through said side surface in a plane substantially parallel to said bottom surface is generally rectangular in shape.

5. The culture vessel of claim 1 wherein said side surface is further disposed so that the cross-sectional area of said lower container portion, for a cross-section taken through said side surface in a plane substantially parallel to said bottom surface, generally continuously decreases as the distance between said cross-sectional plane and said bottom surface increases, whereby liquid located in said lower container portion is restrained from splashing upwardly toward said compartmental volumes.

6. The culture vessel of claim 1 wherein said side surface is further disposed so as to provide a means for grasping said container.

7. The culture vessel of claim 1 wherein said first partitions are sloped so that, when said container is supported on said bottom surface in said upright position, liquid located in said compartmental volumes drains into said lower portion of said container.

8. The culture vessel of claim 7 wherein said first partition has defined therethrough a plurality of openings located so that at least one of said openings is associated with each said compartmental volume, said openings in said first partition being disposed so that, when said container is placed in said upright position, liquid located in said compartmental volumes passes through said first partition openings into said lower portion of said container.

9. The culture vessel of claim 8 wherein the portion of said first partition which forms the bottom wall of each said compartmental volume extends toward said transparent portion of said side wall at a downward angle, so that said first partition slants toward said bottom surface of said container, and wherein said first partition openings are located in the portion of said first partition which is closest to said transparent portion of said side surface.

10. The culture vessel of claim 1 further comprising means for sealing said container opening so that material is prevented from passing through said opening into or out of the interior of said container.

11. The culture vessel of claim 10 wherein said container opening and said means for sealing said opening comprise a neck portion having sealingly engaged thereto a sealing cap, said neck portion being disposed in the surface of said container which has said opening defined therein so as to form a passageway between the interior of said container and the exterior thereof, with said sealing cap being engagable with 12. The culture vessel of claim 1 wherein said first and second partitions and said container opening are further disposed so that material may be introduced through said container opening into preselected compartmental volumes and into said lower container portion without entering nonselected portions of said container.

13. The culture vessel of claim 1 wherein said container opening is located in said side surface.

14. The culture vessel of claim 1 wherein said container opening is located in said top surface.

15. The culture vessel of claim 14 further comprising a channel for directing material from said opening to said lower portion of said container, said channel being disposed so that one end thereof is connected in flow communication with said container opening and the other end of said channel opens into said lower container portion.

16. Apparatus for detecting and culturing microorganisms, said apparatus comprising:

an enclosed container formed by a top surface, a bottom surface disposed so as to stably support said container when said container is placed in an upright position, and a side surface which connects said top surface to said bottom surface, with one of said surfaces having a sealable opening defined therein for introducing material into the volume enclosed by said container, at least one of said surfaces further including a portion which is formed from a flat, transparent material;

a first partition disposed inside said container between said top and bottom surfaces so as to divide the volume enclosed by said container into an upper portion and a lower portion;

at least one second partition disposed inside said container so as to divide said upper portion of said container into two or more compartmental volumes;

said first partition having at least one opening therein between said lower portion and each of said upper compartmental volumes, allowing communication between said lower portion and said upper compartmental volumes, a liquid nutrient medium disposed in said lower container portion; and a plurality of solid nutrient media disposed so that one of said solid media is located in each said compartmental volume, said first and second partitions and said solid nutrient media being configured with respect to said transparent surface portion and to said container opening so that at least a portion of each said solid nutrient medium is viewable through said transparent surface portion and so that material may be introduced through said opening into said lower portion of said container, and said first and second partitions, said side surface and the openings in said first partition all being further disposed so that the liquid nutrient located in said lower container portion is introduced into preselected ones of said compartmental volumes, and makes contact with the solid nutrient media contained therein, by tipping said container at a predetermined angle with respect to said upright position so that such liquid will spill through the at least one opening associated with each such preselected volume.

17. The apparatus of claim 16 wherein said transparent surface portion is included in said side surface of said container and is disposed so that at least a portion of said lower container volume and at least a portion of the solid nutrient medium located in each said compartmental volume is viewable through said transparent surface portion.

18. The apparatus of claim 17 wherein said first partition has defined therethrough a plurality of openings located so that at least one of said openings is associated with each said compartmental volume, said openings in said first partition being disposed so that, when said container is placed in said upright position, liquid located in said compartmental volumes passes through said first partition openings into said lower portion of said container.

19. The apparatus of claim 18 wherein the portion of said first partition which forms the bottom wall of each said compartmental volume extends toward said transparent portion of said side wall at a downward angle, so that said first partition slants toward said bottom surface of said container, and wherein said first partition openings are located in the portion of said first partition which is closest to said transparent portion of said side surface.

20. The apparatus of claim 16 further comprising means for holding each said solid nutrient medium in position within its associated compartmental volume.

21. The apparatus of claim 16 wherein said side surface comprises a front surface and a back surface, with at least said front surface being formed from a flat, transparent material disposed so that said lower container portion and each said solid nutrient medium is viewable through said front surface.

22. The apparatus of claim 21 wherein each said solid nutrient medium is disposed adjacent to said back surface.

23. The apparatus of claim 22 further comprising means for holding each said solid nutrient medium in position relative to said back surface.

24. The apparatus of claim 23 wherein said holding means comprises a plurality of anchoring bars disposed so that at least one of said bars is associated with each said solid nutrient medium, each said anchoring bar being formed as an integral part of said back surface and extending toward said front surface for a predetermined distance into said associated solid nutrient medium.

25. The apparatus of claim 16 wherein said side surface is further disposed so that the cross-sectional area of said lower container portion, for a cross-section taken through said side surface in a plane substantially parallel to said bottom surface, generally continuously decreases as the distance between said cross-sectional plane and said bottom surface increases, whereby liquid located in said lower container portion is restrained from splashing upwardly toward said compartmental volumes.

26. The apparatus of claim 16 wherein said side surface is further disposed so as to provide a means for grasping said container.

27. The apparatus of claim 16 wherein said first and second partitions are further disposed so that, when said container is supported on said bottom surface in said upright position, liquid located in said compartmental volumes drains away from said solid nutrient media into said lower portion of said container.

28. The apparatus of claim 16 further comprising means for sealing said container opening so that material is prevented from passing through said opening into, or out of the interior of said container.

29. The apparatus of claim 28 wherein said container opening and said means for sealing said opening comprise a neck portion having sealingly engaged thereto a sealing cap, said neck portion being disposed in the surface of said container which has said opening defined therein so as to form a passageway between the interior of said container and the exterior thereof, with said sealing cap being engagable with said neck portion so as to prevent material from passing through said passageway.

30. The apparatus of claim 16 wherein said first and second partitions and said container opening are further disposed so that material may be introduced through said opening into preselected compartmental volumes or into said lower container portion without entering nonselected portions of said container.

31. The apparatus of claim 16 wherein said container opening is located in said side surface.

32. The apparatus of claim 16 wherein said container opening is located in said top, surface.

33. The apparatus of claim 32 further comprising a channel for directing material from said opening to said lower portion of said container, said channel being disposed so that one end thereof is connected in flow communication with said container opening and the other end of said channel opens into said lower container portion.

* * * * *